United States Patent

Sawaki et al.

[11] 4,033,754
[45] July 5, 1977

[54] SUBSTITUTED CYCLOHEXENE ESTERS

[75] Inventors: Mikio Sawaki, Takaoka; Isao Iwataki, Odawara; Yoshihiko Hirono, Hiratsuka; Hisao Ishikawa, Odawara, all of Japan

[73] Assignee: Nippon Soda Company Limited, Tokyo, Japan

[22] Filed: Jan. 19, 1976

[21] Appl. No.: 650,140

Related U.S. Application Data

[63] Continuation-in-part of Ser. No. 531,810, Dec. 11, 1974, Pat. No. 3,989,737.

[30] Foreign Application Priority Data

Jan. 22, 1975  Japan .................... 50-8687
Mar. 31, 1975  Japan .................... 50-37884

[52] U.S. Cl. .................... 71/112; 71/88; 71/90; 71/91; 71/92; 71/93; 71/98; 71/103; 71/106; 71/109; 71/110; 71/111; 260/347.5; 260/468 G; 260/468 K; 260/456 R; 260/485 J
[51] Int. Cl.² .................... A01N 9/20; C07C 69/76; C07C 69/82; C07C 69/83
[58] Field of Search .................... 260/475 R; 71/112

[56] References Cited
FOREIGN PATENTS OR APPLICATIONS 2,439,104  3/1975  Germany Primary Examiner—Jane S. Myers
Attorney, Agent, or Firm—George B. Oujevolk

[57] ABSTRACT

A compound of the general formula

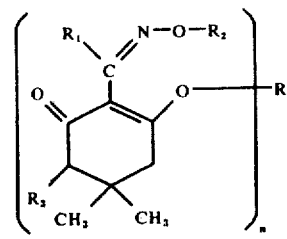

wherein
$R_1$ is lower alkyl having six or less carbon atoms,
$R_2$ is lower alkyl having six or less carbon atoms or lower alkenyl having six or less carbon atoms,
$R_3$ is hydrogen or lower alkoxycarbonyl having six or less carbon atoms,
R is aliphatic or aromatic ester residue of dibasic or tribasic acid and
n is 2 or 3;
is useful as herbicide.

24 Claims, No Drawings

SUBSTITUTED CYCLOHEXENE ESTERS

This application is a continuation-in-part of our pending application Ser. No. 531,810 filed Dec. 11, 1974, now U.S. Pat. No. 3,989,737.

DETAILED DESCRIPTION OF THE INVENTION

This invention relates to novel compounds of cyclohexene-esters, to a process for the preparation thereof and their uses as selective herbicide.

More particularly, this invention is directed to compositions and methods employing, as an active herbicidal ingredient, at least one compound of the formula:

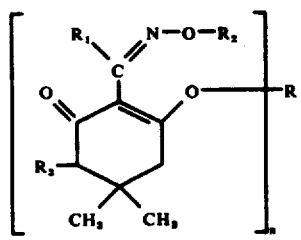

wherein
$R_1$ is lower alkyl having six or less carbon atoms,
$R_2$ is lower alkyl having six or less carbon atoms or lower alkenyl having six or less carbon atoms,
$R_3$ is hydrogen or lower alkoxycarbonyl having six or less carbon atoms,
R is aliphatic or aromatic ester residue of dibasic or tribasic acid and
n is 2 or 3.

Preferred for use according to this invention because they are effective as herbicides at lower rates of application and stable are compounds of the formula

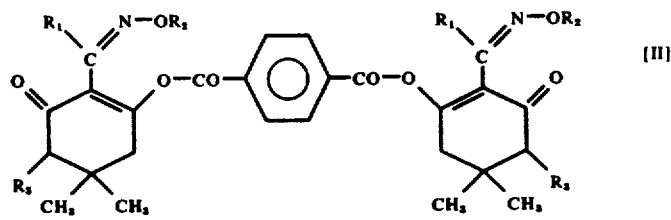

wherein
$R_1$ is ethyl or propyl,
$R_2$ is ethyl or allyl and
$R_3$ is hydrogen or methoxycarbonyl.

Especially preferred for use because of their herbicidal effectiveness are:
bis[2-(N-allyloxybutyrimidoyl)-5,5-dimethyl-3-oxo-1-cyclohexene-1-yl]-terephthalate,
bis[2-(N-allyloxybutyrimidoyl)-5,5-dimethyl-3-oxo-1-cyclohexene-1-yl]-isophthalate,
bis[2-(N-allyloxybutyrimidoyl)-5,5-dimethyl-3-oxo-1-cyclohexene-1-yl]-1,3-benzenedisulfonate,
bis[2-(N-allyloxybutyrimidoyl)-4-methoxycarbonyl-5,5-dimethyl-3-oxo-1-cyclohexene-1-yl]-terephthalate.

The compounds of this invention can be prepared in accordance with the following equation:

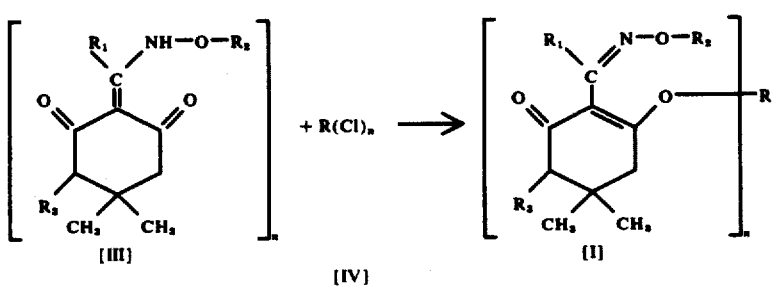

wherein $R_1$, $R_2$, $R_3$ and n are previously defined.

The starting material [III] can be prepared in accordance with the following equations:

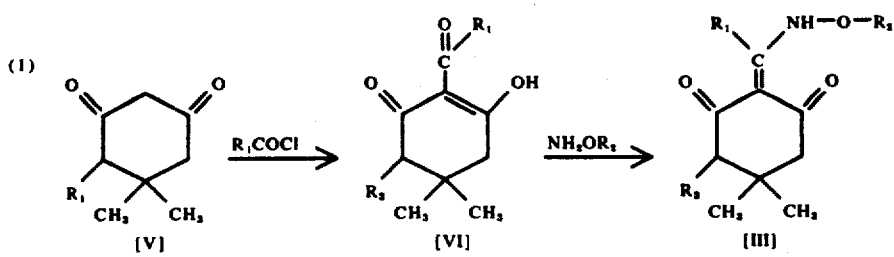

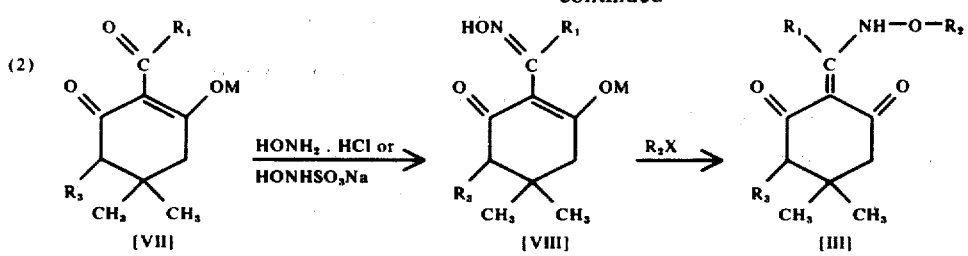

wherein
M is hydrogen or alkali metal atom (preferably M is sodium),
X is halogen. With respect to the above formula [III], the said compound has the following isomer because of tautomerism:

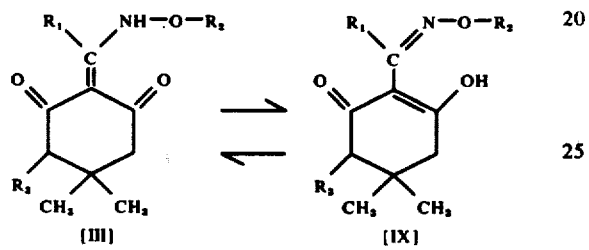

In practical method, first of all alkali metal salt of the starting compound [III] are prepared by treating it with sodium or potassium hydroxide in an organic solvent.

The said alkali metal salt is made to react with the compound of general formula [IV] in an inert solvent after separating it from the reaction mixture or as it is. Otherwise, the compound [III] is made to react with the compound [IV] in the presence of alkali metal salts such as sodium or potassium hydroxide.

As an inert solvent, acetone, ether, alcohol, benzene, toluene, chloroform and ethyl acetate etc. are used.

Ordinarily, temperatures from the range of −20° C to the boiling point of the solvent, and preferably below room temperature, are satisfactorily employed for the above reaction and the reaction terminates between about 15 minutes and 3 hours.

As the acid chlorides of the formula [IV] used as starting materials, the chlorides of the following dibasic or tribasic acid can be employed:
a. aliphatic: malonic acid, succinic acid, glutaric acid, adipic acid, azelaic acid, sebacic acid, methylmalonic acid, methylsuccinic acid, maleic acid, phthalic acid, cyclohexene-1,4-dicarboxylic acid etc.,
b. phthalic acid derivatives: terephthalic acid, isophthalic acid, phthalic acid, 1,3,5-benzenetricarboxylic acid and these compounds substituted with alkyl or halogen, tetrahydrophthalic acid, bicyclo[2,2,1]heptane-2,3-dicarboxylic acid (3,6-methylenetetrahydrophthalic acid), 7-oxabicyclo[2,2,1]heptane-2,3-dicarboxylic acid etc;
c. sulfonic acid:
1,3-benzenedisulfonic acid, 1,3,5-benzenetrisulfonic acid,

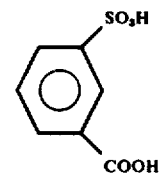

and these compound substituted with alkyl or halogen etc.

In order that the invention may be better understood, the following examples are given:

EXAMPLE 1

Manufacture of the compound of formula

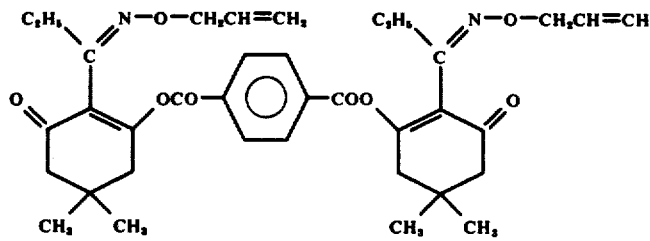

(Compond No. 1)

After finishing the reaction, the employed solvent, if necessary, is replaced with the other solvent and then, the reaction mixture is washed with alkaline solution and water and dried, and further, solvent is distilled off under reduced pressure, thereby the crude product is obtained as crystal or liquid.

The crude product can be purified by recrystallization or column chromatography. A structural formula of the resulting purified compound can be confirmatively identified by means of an elementary analysis, NMR spectrum or IR spectrum etc.

5 g of 2-(1-allyloxyaminopropylidene)-5,5-dimethyl-cyclohexane-1,3-dione were dissolved in 50 ml of acetone and 2 ml of aqueous solution containing 0.9 g of dissolved sodium hydroxide was added to it, the resulting solution was stirred at room temperature for 1.5 hours and thereby sodium salt of 2-(1-allyloxyaminopropylidene)-5,5-dimethylcyclohexane-1,3-dione was formed.

After cooling the resulting solution, 1.6 g of terephthalic acid dichloride were added slowly to said solution at a temperature of 0°-5° C, and it was stirred for 30 minutes at a temperature of 0°–5° C and further for additional two hours at room temperature.

After finishing the reaction, the precipitated sodium chloride was removed. Acetone was distilled off, the residual material was poured into 100 ml of water and it was extracted with chloroform.

The resulting chloroform layer was washed with aqueous solution containing 5% of sodium hydroxide and with water. The said chloroform layer was dried with sodium sulfate and chloroform was distilled off. By recrystallizing the resulting residual material from acetone, 4.3 g of the desired product having a melting point of 122°–125° C were obtained.

EXAMPLE 2

Manufacture of the compound of the formula

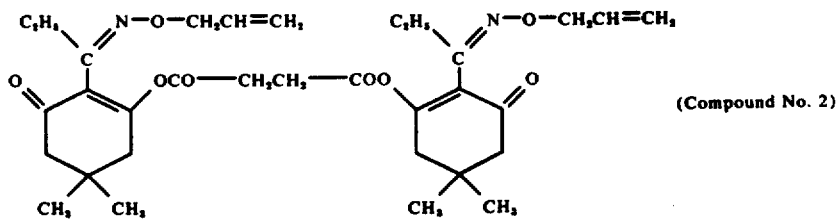

(Compound No. 2)

5 g of 2-(1-allyloxyaminopropylidene)-5,5-dimethylcyclohexane-1,3-dione were dissolved in 50 ml of acetone and 2 ml of aqueous solution containing 0.9 g of dissolved sodium hydroxide was added to it, the resulting solution was stirred at room temperature for one hours and thereby sodium salt of 2-(1-allyloxyaminopropylidene)-5,5-dimethylcyclohexane-1,3-dione was formed. After cooling the resulting solution, 1.5 g of succinic acid dichloride were added slowly to said solution, and it was stirred for 30 minutes at a temperature of 0°–5° C and further for additional two hours at room temperature. After finishing the reaction, the precipitated sodium chloride was removed, acetone was distilled off, the residual material was poured into 100 ml of water and was extracted with chloroform.

The resulting chloroform layer was washed with aqueous solution containing 5% of sodium hydroxide and with water. The said chloroform layer was dried with sodium sulfate and chloroform was distilled off. By recrystallizing the resulting residual material from n-hexane, 2.5 g of the desired product having a melting point of 71°–74° C were obtained.

EXAMPLE 3

Manufacture of the compound of the formula

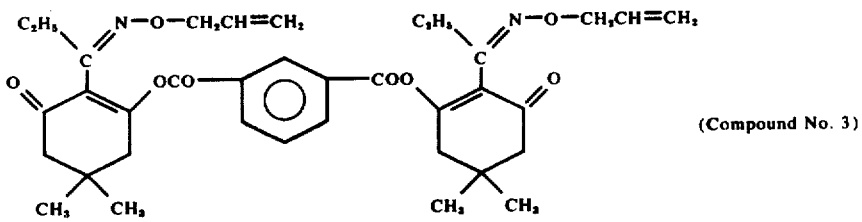

(Compound No. 3)

5 g of 2-(1-allyloxyaminopropylidene)-5,5-dimethylcyclohexane-1,3-dione were dissolved in 40 ml of acetone and 2 ml of aqueous solution containing 0.8 g of dissolved sodium hydroxide was added to it, the resulting solution was stirred at room temperature for one hour and thereby sodium salt of 2-(1-allyloxyaminopropylidene)-5,5-dimethylcyclohexane-1,3-dione was formed. Being concentrated, acetone and water of the reaction solution were distilled off and further 40 ml of acetone were added to the resulting residual material. Under cooling by ice water, 1.5 g of adipic acid chloride was added dropwise to the acetone solution and it was stirred at room temperature for one hour. After distilling acetone, the reaction mixture was poured into ice-water and it was extracted for two times with the mixture of n-hexane and ether (1:1). The organic solvent layer was washed with aqueous solution containing 10 weight % of sodium hydroxide, further with water for two times and it was dried with magnesium sulfate.

By distilling organic solvent under reduced pressure, 3.7 g of the desired product having a melting point of 52°–54° C were obtained.

EXAMPLE 4

Manufacture of the compound of the formula

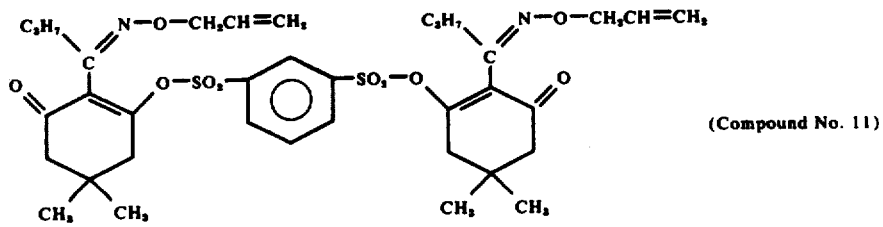

(Compound No. 11)

The same reaction procedures as Example 1 were carried out by using 3.9 g of 2-(1-allyloxyaminobutylidene)-5,5-dimethylcyclohexane-1,3-dione and 2.5 g of m-benzenesulfonylcychloride, and thereby 3.5 g of the desired product having a refractive index $n_D^{28}$ 1.5277 were obtained.

EXAMPLE 6

Manufacture of the compound of the formula

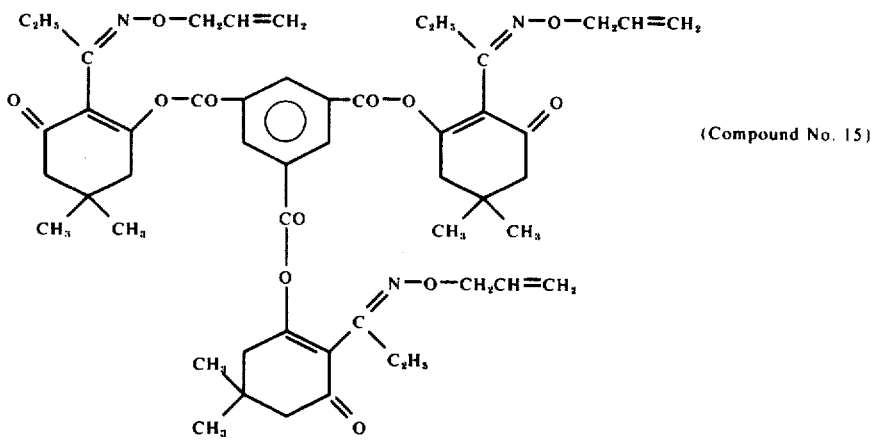

(Compound No. 15)

EXAMPLE 5

Manufacture of the compound of the formula

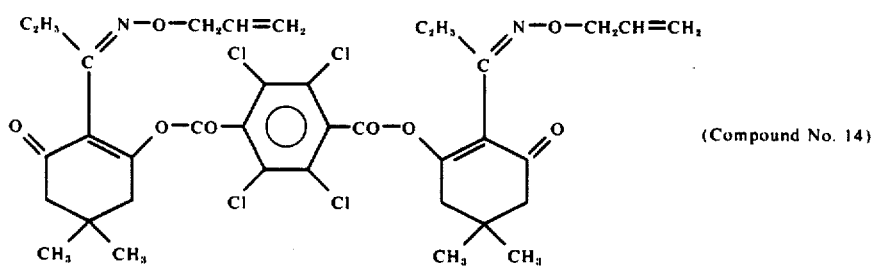

(Compound No. 14)

4.5 g of 2-(allyloxyaminopropylidene)-5,5-dimethylcyclohexane-1,3-dione were dissolved in 50 ml of acetone and 2 ml of aqueous solution containing 0.7 g of dissolved sodium hydroxide was added to it, the solution was stirred at room temperature for one hour and thereby sodium salt of 2-(1-allyloxyaminopropylidene)-5,5-dimethylcyclohexane-1,3-dione was formed. After cooling the solution, 3 g of 2, 3, 5, 6-tetrachlorotelephthalic acid dichloride were added slowly to it at a temperature of 0°-5° C, and it was stirred for 30 minutes at the same temperature and further for additional two hours at room temperature. After finishing the reaction, the precipitated sodium chloride was removed and acetone was distilled off. The residual material was poured into aqueous solution containing 4 weight % of sodium hydroxide and the insoluble white crystals were filtered. After washing said crystals with ether 5.5 g of the desired product having a decomposition point of 132°-133° C as white dust were obtained.

The same reaction procedures at Example 1 were carried out by using 4.5 g of 2-(1-allyloxyaminopropylidene)-5,5-dimethylcyclohexane-1,3-dione and 1.6 g of trimesoyl chloride, and the reaction mixture was extracted with ether instead of chloroform and thereby 4 g of the desired product having a refractive index $n_D^{23}$ 1.5246 as an oily substance were obtained.

EXAMPLE 7

Manufacture of the compound of the formula

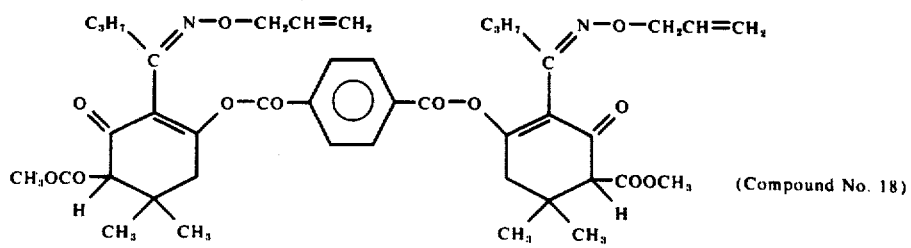

(Compound No. 18)

10 g of 2-(1-N-allyloxyaminobutylidene)-4-methoxycarbonyl-5,5-dimethylcyclohexane-1,3-dione were dissolved in 80 ml of acetone and 8 ml of aqueous solution containing 1.23 g of dissolved sodium hydroxide was added to it. Under cooling the resulting solution, 3.14 g of terephthalic acid dichloride dissolved in 30 ml of acetone were added dropwise to it and, after stirring at room temperature for one hour, the precipitates were removed by filtration and acetone was distilled off.

The residual material was extracted with chloroform, and then the chloroform layer was washed with aqueous solution containing of sodium hydroxide of 5 weight % and further with water.

By distilling chloroform after drying the chloroform layer with sodium sulfate 8.4 g of the desired product having a refractive index $n_D^{23}$ 1.5215 as an oily material were obtained.

Examples of the compounds which can be used in the present invention are listed in Table 1.

Table 1

| Compound No. | Structural Formula | Chemical Name | Physical Constant |
|---|---|---|---|
| 1 | (structure) | bis[2-N-allyloxypropionimidoyl)-5,5-dimethyl-3-oxo-1-cyclohexene-1-yl-]terephthalate | m.p. 122–125° C |
| 2 | (structure) | bis[2-(N-allyloxypropionimidoyl)-5,5-dimethyl-3-oxo-1-cyclohexene-1-yl]succinate | m.p. 71–74° C |
| 3 | (structure) | bis[2-N-allyloxypropionimidoyl)-5,5-dimethyl-3-oxo-1-cyclohexene-1-yl]-isophthalate | $n_D^{25.5}$ 1.5233 |
| 4 | (structure) | bis[2-(N-allyloxypropionimidoyl)-5,5-dimethyl-3-oxo-1-cyclohexene-1-yl]-phthalate | $n_D^{20}$ 1.5292 |
| 5 | (structure) | bis[2-(N-allyloxybutyrimidoyl)-5,5-dimethyl-3-oxo-1-cyclohexene-1-yl]-terephthalate | m.p. 98–100° C |
| 6 | (structure) | bis[2-(N-allyloxybutyrimidoyl)-5,5-dimethyl-3-oxo-1-cyclohexene-1-yl]-isophthalate | $n_D^{20}$ 1.5243 |
| 7 | (structure) | bis[2-(N-allyloxypropionimidoyl)-5,5-dimethyl-3-oxo-1-cyclohexene-1-yl]-azelate | $n_D^{24.5}$ 1.5048 |
| 8 | (structure) | bis[2-(N-allyloxybutyrimidoyl)-5,5-dimethyl-3-oxo-1-cyclohexene-1-yl]-azelate | $n_D^{20}$ 1.4993 |
| 9 | (structure) | bis[2-(N-allyloxybutyrimidoyl)-5,5-dimethyl-3-oxo-1-cyclohexene-1-yl]-adipate | $n_D^{20}$ 1.5038 |

Table 1-continued

| Compound No. | Structural Formula | Chemical Name | Physical Constant |
|---|---|---|---|
| 10 | | bis[2-(N-allyloxypropionimidoyl)-5,5-dimethyl-3-oxo-1-cyclohexene-1-yl]-adipate | m.p. 52–54° C |
| 11 | | bis[2-(N-allyloxybutyrimidoyl)-5,5-dimethyl-3-oxo-1-cyclohexene-1-yl]-1,3-benzenedisulfonate | $n_D^{20}$ 1.5277 |
| 12 | | bis[2-(N-allyloxypropionimidoyl)-5,5-dimethyl-3-oxo-1-cyclohexene-1-yl]-1,3-benzenedisulfonate | $n_D^{20}$ 1.5340 |
| 13 | | bis[2-(N-allyloxypropionimidoyl)-5,5-dimethyl-3-oxo-1-cyclohexene-1-yl]-1,4-cyclohexanedicarboxylate | $n_D^{20}$ 1.5135 |
| 14 | | bis[2-(N-allyloxypropionimidoyl)-5,5-dimethyl-3-oxo-1-cyclohexene-1-yl]-2,3,5,6-tetrachloroterephthalate | m.p. 132–133° C (decomposition) |
| 15 | | tris[2-(N-allyloxypropionimidoyl)-5,5-dimethyl-3-oxo-1-cyclohexene-1-yl]-1,3,5-benzenetricarboxylate | $n_D^{20}$ 1.5246 |
| 16 | | bis[2-(N-allyloxybutyrimidoyl)-5,5-dimethyl-3-oxo-1-cyclohexene-1-yl]-2,3,5,6-tetrachloroterephthalate | m.p. 97–98° C |
| 17 | | [2-(N-allyloxypropionimidoyl)-5,5-dimethyl-3-oxo-1-cyclohexen-1-yl]-3-[2-(N-allyloxypropionimidoyl)-5,5-dimethyl-3-oxo-1-cyclohexenyl]-oxysulfonylbenzoate | $n_D^{20}$ 1.5250 |

Table 1-continued

| Compound No. | Structural Formula | Chemical Name | Physical Constant |
|---|---|---|---|
| 18 | (structure) | bis[2-(N-allyloxybutyrimidoyl)-4-methoxycarbonyl-5,5-dimethyl-3-oxo-1-cyclohexene-1-yl]-terephthalate | $n_D^{20}$ 1.5215 |
| 19 | (structure) | bis[2-(N-allyloxypropionimidoyl)-4-methoxycarbonyl-5,5-dimethyl-3-oxo-cyclohexene-1-yl]-terephthalate | $n_D^{20}$ 1.5282 |

Hereinafter, the compounds of this invention are represented by Compound No. in Table 1.

As mentioned previously, it has been found that the compounds of the invention possess superior herbicidal activity. The paragraphs which follow described in more detail the utility of this invention.

The compounds of the invention are particularly effective in the control of grass weeds such as annual bluegrass (Poa annua L.), water foxtail (Alopecurus aequalis Sobol), large crabgrass (Digitaria adscendens Henr.), green foxtail (Seturia viridis Beauv), wild oat (Avena fatua L) etc. and they hardly injure broad leaf crops such as adzuki bean (Phaseolus angularis W. F. Wight) and soy bean (Glycine max Merrill) and sugar beets (Beta vulgaris L.) which easily suffer phyto-toxicity. Namely, the compound of the invention are the selective herbicide.

It is already known that 4-acetoxy-6-methyl-α-pyrone derivative having (N-alkoxy or alkenyloxy)acetamidoyl group derivatives have herbicidal properties as shown in Offenlegungsschrift No. 2,252,818.

But in order to destroy completely the said grass weeds, a large amount of the above herbicidal chemical is required and this is one drawback for above mentioned herbicidal compound.

In the event of employing the compounds of this invention as a herbicide, even a chemical amount less than one-forth of above known compound may exhibit a perfect prevention and extermination of weeds, namely, the compounds of this invention are about 4 times effective compared with known compounds.

In case of foliar treatment using the compounds of the present invention, even the same amount of chemical which kills completely barnyard grass of grass weeds gives no damages to broadleaf plants such as radish (Raphanus sativus L.), soy bean, garden pea (Pisum sativum L), spinach (Spinacia oleracea L.) sugar beets and carrot (Daucus carota L.) at all, and in case of soil treatment before germination, even the same amount of chemicals which prevents large crabgrass germinating gives no damages to seeds of brad leaf plants at all.

As mentioned above, a security to the broadleaf crop against phytotoxicity of the herbicide is extremely high and as to its application, in the other words, its applicable time, its applying location and its applying concentration, it has a very broad extent and it can be used in a wider extent.

It is another advantage of the present invention that a residual toxicity in the soil or the plant and an acute toxicity for warm blooded animals and fish are not feared because the said compounds can be used with a low chemicals concentration.

The compounds of this invention can be applied directly to the soil as preemergence treatment or to plant foliage, as post-emergence treatment, or they can be mixed intimately with the soil, preferably pre-emergence treatment to the soil, and may be applied to soil or plant foliar at rates of 50-1000 g per 10 are, preferably 50-200 g per 10 are, more preferably about 100 g per 10 are.

The method of the present invention comprehends the employment of a liquid or solid composition containing one or more of the present comounds as an active ingredient.

The active ingredient of this invention may be formulated by mixing with suitable carriers in a form generally used in agricultural chemicals such as wettable powders, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, benzene, xylene, cyclohexane, cyclohexanone, dimethylformamide, alcohol, acetone, and others are used. Sometimes surface active agent is added in order to give a homogeneous and stable formulation.

The compounds of this invention also can be applied admixed with other chemicals which are used in agronomic and horticultural management and are compatible with the compounds of this invention. Such chemicals can be, but are not restricted to, the classes of chemicals commonly known as plant nutrients, fertilizers, insecticide acaricides, fungicides, herbicides and nematocides.

As for known herbicides it is recommended that the compound of the present invention is applied admixed with the herbicidal compound selected from the group consisting of N-(3-chloro-4-methoxyphenyl)-N',N'-dimethylurea,
N-(3,4-dichlorophenyl)-N',N'-dimethylurea,
N-(3,4-dichlorophenyl)-N'-methoxy-N'-methylurea,
1,3-dimethyl-(3-benzothiazole-2-yl)urea,
1,3-dimethyl-3-(5-methylbenzothiazole-2-yl)urea,
1,3-dimethyl-3-(5-t-butylbenzothiazole-2-yl)urea, 1,1,3-trimethyl-3-(5-methylbenzothiazole-2yl)urea,
1,1,3-trimethyl-3-(5-ethylbenzothiazole-2-yl)urea,
1,3-dimethyl-3-(5,7-dimethylbenzothiazole-2-yl)urea,
1,1,3-trimethyl-3-(5,7-dimethylbenzothiazole-2-yl)urea,
2-chloro-4,6-diethylamino-1,3,5-triazine,
2-chloro-4-ethylamino-6-isopropylamino-1,3,5-triazine,
2-chloro-4,6-diisopropylamino-1,3,5-triazine,
2-methylmercapto-4-ethylamino-6-isopropylamino-1,3,5-triazine,
2-methylmercapto-4-diisopropylamino-1,3,5-triazine,
3-methoxycarbonylaminophenyl-N-(3'-methylphenyl)-carbamate,
methyl N-(3,4-dichlorophenyl)carbamate,
isopropyl N-(3-chlorophenyl)carbamate,
S-(4-chlorobenzyl)-N,N-diethylthiol carbamate,
4'-nitro-2,4-dichloro-diphenyl ether,
4-nitro-2,4,6-trichloro-diphenyl ether,
2-methyl-4-chloro-phenoxyacetic acid,
2,4-dichloro-phenoxyacetic acid,
3-isopropyl-2,1,3-benzothiadiazine-4-one-2,2-dioxide,
and 1-phenyl-4-amino-5-chloro-pyridazine, The concentrations of the active ingredients in the herbicidal composition of this invention vary according to type of formulation, and they are, for example, used in a range of 5 – 80 weight percent, preferably 10 – 60 weight percent, in wettable powder, 5 – 70 weight percent, preferably 20 – 60 weight percent, in emulsifiable concentrates, and 0.5 – 30 weight percent, preferably 1 – 10 weight percent in dust formulation.

Thus, a wettable powder or an emulsifiable concentrate produced thereto is diluted with water to a specific concentration and thereby, it is used as a liquid suspension or a liquid emulsion for treating soils or plant foliars. Furhter, a dust formulation is directly used for the soil treatment or the foliar treatment.

The non-limiting exaples for the herbicidal composition are illustrated as follows:

EXAMPLE 8

Wettable Powder

| | Parts by weight |
|---|---|
| Compound No. 2 | 50 |
| Diatomaceous earth | 21 |
| Sodium alkylsulfate | 8 |
| Talc | 21 |

These are mixed homogeneously and reduced to fine particles. Consequently, wettable powder containing 50% of active ingredient is obtained. In practical use, it is diluted to a certain concentration with water and is sprayed as a suspension.

EXAMPLE 9

Emulsifiable Concentrate

| | Parts by weight |
|---|---|
| Compound No. 1 | 40 |
| Xylene | 35 |
| Dimethylformamide | 15 |

These are mixed and dissolved.

Consequently, emulsifiable concentrate containing 40% of the active ingredient is obtained. In practical use, it is diluted to certain concentration with water and then is sprayed an emulsion.

EXAMPLE 10

Granular Formulation

| | Parts by weight |
|---|---|
| Compound No. 3 | 7 |
| Talc | 38 |
| Bentonite | 10 |
| Clay | 38 |
| Sodium alkylsulfate | 7 |

These are mixed homogeneously and reduced to fine particles. Fine particles are made into granules having the diameter in the range of 0.5 – 1.0 mm by granulator.

Consequently, granular formulation containing 7% of the active ingredient is obtained. In practical use it is directly applied.

The superior herbicidal effect of the novel compounds of this invention is clearly understood by the following test.

Test 1

Pre-emergence treatment (soil treatment in paddy condition)

About 60 seeds of barnyard grass were planted in a pot having 60 square centimeters surface area and covered slightly with soil. Water was poured into the pot until the surface of soil became wet.

10 ml of an aqueous emulsion prepared by diluting an emulsifiable concentrate with water to a specified concentration was sprayed on the pot. The pots were kept in a green house and water was added to the pots daily in order to keep the water level. Three weeks after spraying, the degrees of damage to the plant were observed and estimated by the values of 0 – 5 which have the following meanings:

0: no effect
1: partial plant slightly injured
2: plant slightly injured
3: plant moderately injured
4: plant severely injured
5: plant completely killed or no germination The results were shown in Table 2.

Table 2

| Test Compound NO. | Application rate (g/10 ares) | | |
|---|---|---|---|
| | 125 | 60 | 30 |
| 1 | 5 | 5 | 5 |
| 2 | 5 | 5 | 5 |
| 3 | 5 | 5 | 5 |
| 4 | 5 | 5 | 5 |
| 5 | 5 | 5 | 5 |
| 6 | 5 | 5 | 5 |
| 9 | 5 | 5 | 5 |
| 18 | 5 | 5 | 5 |
| Comparative compound O—CO—CH₃ structure* | 5 | 3 | 1 |
| Untreated | 0 | | |

*Offenlegungschrift 2252818

Test 2

Post-emergence treatment
(foliar treatment in paddy condition)

About 50 seeds of barnyard grass were planted in a pot having 60 square centimeters and covered slightly with soil. Said pot was filled with water to about 3 cm above the surface of the soil when the plant was grown to first leafstage.

An aqueous emulsion prepared by diluting an emulsifiable concentrate with water to a specified concentration was sprayed on the pot. The pots were kept in a green house and water was added to the pot daily in order to keep the water level. Two weeks after spraying, the degrees of damage to the test plant was observed and estimated by the values of 0 – 5 which have the same meaning as those of Test 1.

The results were shown in Table 3.

Table 3

| Test Compound No. | Application rate (g/10 ares) | | |
|---|---|---|---|
| | 250 | 125 | 60 |
| 2 | 5 | 5 | 3 |
| 3 | 5 | 5 | 5 |
| 5 | 5 | 5 | 5 |
| 6 | 5 | 5 | 5 |
| 9 | 5 | 5 | 5 |
| 18 | 5 | 5 | 5 |
| Comparative compound (O—CO—CH$_3$, NOC$_2$H$_5$, CH$_3$, CH$_3$ pyranone structure) | 5 | 4 | 2 |
| Untreated | | | 0 |

Test 3

Pre-emergence treatment

Seeds of large crab-grass were planted in a pot having 100 square centimeters. An aqueous emulsion prepared by diluting an emulsifiable concentrate with water to a specified concentration was sprayed on the surface of the soil before emergence. The pots were kept in a green house. 21 days after spraying, the degrees of damage to the test plants were observed and estimated by the value of 0 – 5 which have the same meanings as those of Test 1.

The results were shown in Table 4.

Table 4

| Test Compound No. | Application rate (g/10 ares) | | | |
|---|---|---|---|---|
| | 250 | 125 | 60 | 30 |
| 1 | 5 | 5 | 5 | 3 |
| 2 | 5 | 5 | 4 | 3 |
| 3 | 5 | 5 | 5 | 4 |
| 4 | 5 | 5 | 4 | 3 |
| 5 | 5 | 5 | 5 | 5 |
| 6 | 5 | 5 | 5 | 5 |
| 9 | 5 | 5 | 5 | 5 |
| Comparative compound (O—COCH$_3$, NOC$_2$H$_5$, CH$_3$, CH$_3$ pyranone structure) | 5 | 3 | 1 | 0 |
| Untreated | | | | 0 |

Test 4

Post-emergence treatment (foliar treatment)

Seeds of large crab-grass was planted in a pot having 100 square centimeters. When plants became 2 – 4 leaves stage, an aqueous emulsion prepared by diluting an emulsifiable concentrate with water to a specified concentration was sprayed on the foliar of the test plant at a rate of 100 liters per 10 are. The plants were kept in a green house.

21 days after spraying, the degrees of damage to the test plant were observed and estimated by the value of 0 – 5 which have the same meanings as those of Test 1.

The results were shown in Table 5.

Table 5

| Test Compound No. | Application rate (g/10 ares) | | |
|---|---|---|---|
| | 200 | 100 | 50 |
| 2 | 5 | 5 | 4 |
| 3 | 5 | 5 | 4 |
| 4 | 5 | 5 | 4 |
| 5 | 5 | 5 | 4 |
| 6 | 5 | 5 | 4 |
| 9 | 5 | 5 | 4 |
| 18 | 5 | 5 | 4 |
| Comparative compound (O—COCH$_3$, NOC$_2$H$_5$, CH$_3$, CH$_3$ pyranone structure) | 4 | 2 | 1 |
| Untreated | | | 0 |

What is claimed is:

1. A compound of the general formula

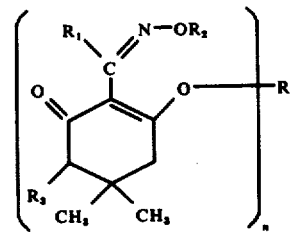

wherein
R$_1$ is lower alkyl having six or less carbon atoms,
R$_2$ is selected from the group consisting of lower alkyl having six or less carbon atoms and lower alkenyl having six or less carbon atoms,
R$_3$ is selected from the group consisting of hydrogen and lower alkoxycarbonyl having six or less carbon atoms,
R is the residue of a benzene di- or tricarboxylic acid which may be substituted by alkyl or halogen, and
n is 2 or 3.

2. A compound of the general formula

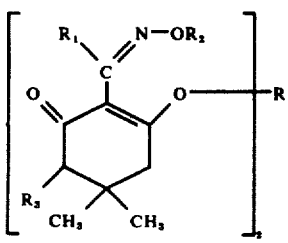

wherein
R₁ is selected from the group consisting of ethyl and propyl,
R₂ is selected from the group consisting of ethyl and allyl,
R₃ is selected from the group consisting of hydrogen and methoxycarbonyl, and R is the residue of benzene dicarboxylic acid which may be substituted by alkyl or halogen.

3. A compound of the general formula

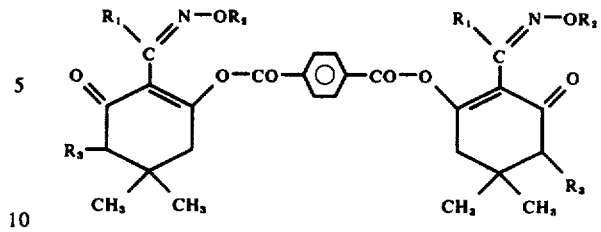

wherein
R₁ is selected from the group consisting of ethyl and propyl,
R₂ is selected from the group consisting of ethyl and allyl, and
R₃ is selected from the group consisting of hydrogen and methoxycarbonyl.

4. A compound of the formula

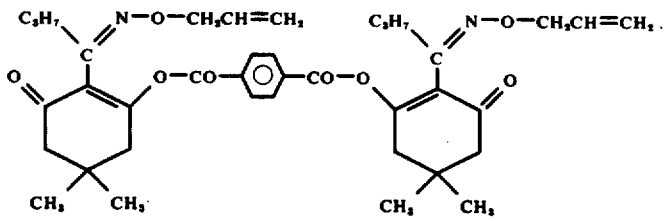

5. A compound of the formula

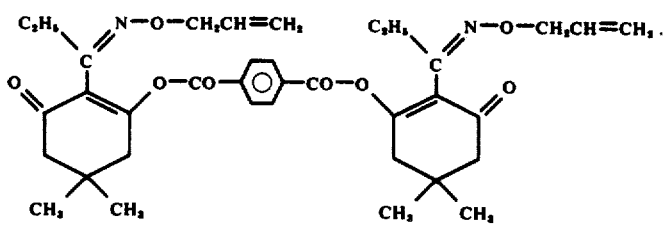

6. A compound of the formula

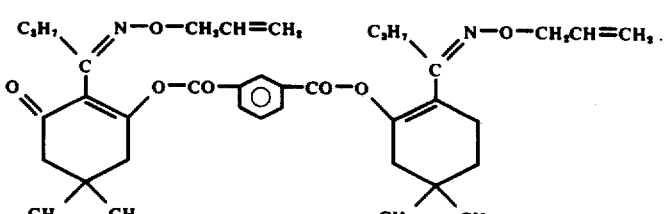

7. A compound of the formula

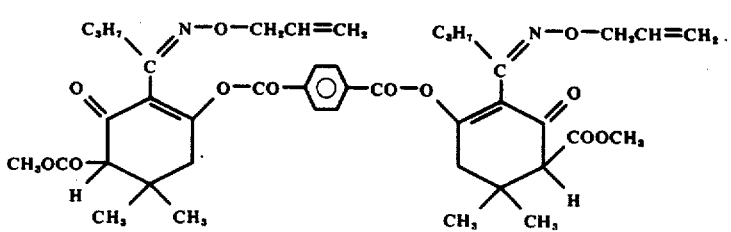

8. A compound of the formula

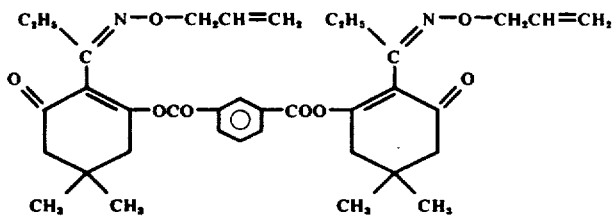

9. A herbicidal composition comprising an inert carrier and a herbicidally effective amount of a compound of claim 1.

10. A herbicidal composition comprising an inert carrier and a herbicidally effective amount of a compound of claim 2.

11. A herbicidal composition comprising an inert carrier and a herbicidally effective amount of a compound of claim 3.

12. A herbicidal composition comprising an inert carrier and a herbicidally effective amount of a compound of claim 4.

13. A herbicidal composition comprising an inert carrier and a herbicidally effective amount of a compound of claim 5.

14. A herbicidal composition comprising an inert carrier and a herbicidally effective amount of a compound of claim 6.

15. A herbicidal composition comprising an inert carrier and a herbicidally effective amount of a compound of claim 7.

16. A herbicidal composition comprising an inert carrier and a herbicidally effective amount of the compound of claim 8.

17. A method for the control of weeds comprising applying a compound of claim 1 in an amount sufficient to exert herbicidal action to a locus to be protected.

18. A method for the control of weeds comprising applying a compound of claim 2 in an amount sufficient to exert herbicidal action to a locus to be protected.

19. A method for the control of weeds comprising applying a compound of claim 3 in an amount sufficient to exert herbicidal action to a locus to be protected.

20. A method for the control of weeds comprising applying a compound of claim 4 in an amount sufficient to exert herbicidal action to a locus to be protected.

21. A method for the control of weeds comprising applying a compound of claim 5 in an amount sufficient to exert herbicidal action to a locus to be protected.

22. A method for the control of weeds comprising applying a compound of claim 6 in an amount sufficient to exert herbicidal action to a locus to be protected.

23. A method for the control of weeds comprising applying a compound of claim 7 in an amount sufficient to exert herbicidal action to a locus to be protected.

24. A method for the control of weeds comprising applying a compound of claim 8 in an amount sufficient to exert herbicidal action to a locus to be protected.

* * * * *